US010369278B2

(12) United States Patent
Schabbach et al.

(10) Patent No.: US 10,369,278 B2
(45) Date of Patent: Aug. 6, 2019

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 485 days.

(21) Appl. No.: 14/916,667

(22) PCT Filed: Sep. 2, 2014

(86) PCT No.: PCT/EP2014/068597
§ 371 (c)(1),
(2) Date: Mar. 4, 2016

(87) PCT Pub. No.: WO2015/032743
PCT Pub. Date: Mar. 12, 2015

(65) Prior Publication Data
US 2016/0213838 A1 Jul. 28, 2016

(30) Foreign Application Priority Data
Sep. 5, 2013 (EP) ..................... 13183152

(51) Int. Cl.
*A61M 5/32* (2006.01)
*A61M 5/46* (2006.01)
*A61M 5/158* (2006.01)

(52) U.S. Cl.
CPC .......... *A61M 5/158* (2013.01); *A61M 5/3287* (2013.01); *A61M 5/46* (2013.01);
(Continued)

(58) Field of Classification Search
CPC ......... A61M 2005/14252; A61M 2005/14268; A61M 2005/1583; A61M 2005/1585; A61M 5/327; A61M 5/32; A61M 5/46
See application file for complete search history.

(56) References Cited

U.S. PATENT DOCUMENTS 3,450,081 A * 6/1969 Rabinow ................ D05B 55/14
112/221
3,521,676 A 7/1970 MacIsaac
(Continued)

FOREIGN PATENT DOCUMENTS

DE 1907569 10/1969
GB 813439 5/1959
(Continued)

OTHER PUBLICATIONS

Definition of parallel (Merriam-Webster Apr. 20, 2018).*
(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

The invention relates to a drive mechanism (9) for a needle insertion arrangement (1), the drive mechanism (9) comprising a rotatable wheel (10) with a notch (12) having a closed curve geometry comprising a curved section (12.1) and a linear section (12.2), wherein at least one cross beam (15, 16) is movably arranged and engageable to an injection needle (2) to move it between a retracted position (RP) and an extended position (EP), wherein the cross beam (15, 6) comprises a cam (15.1, 16.1) adapted to engage the notch (12).

19 Claims, 11 Drawing Sheets

(52) U.S. Cl.
CPC ............... *A61M 2005/1583* (2013.01); *A61M 2005/1585* (2013.01)

(56) References Cited

U.S. PATENT DOCUMENTS

| | | | | |
|---|---|---|---|---|
| 4,658,744 | A * | 4/1987 | Takauchi | D05B 69/24 112/448 |
| 5,738,004 | A * | 4/1998 | Townsend | A22C 17/0053 99/487 |
| 6,530,900 | B1 * | 3/2003 | Daily | A61M 5/14248 604/132 |
| 9,913,970 | B2 * | 3/2018 | Arami | A61K 9/0021 |
| 2005/0245956 | A1 * | 11/2005 | Steinemann | A61M 5/158 606/185 |
| 2006/0253086 | A1 * | 11/2006 | Moberg | A61M 5/1413 604/272 |
| 2007/0049865 | A1 * | 3/2007 | Radmer | A61M 5/14248 604/93.01 |
| 2008/0051711 | A1 * | 2/2008 | Mounce | A61J 1/1406 604/131 |
| 2008/0051714 | A1 * | 2/2008 | Moberg | A61M 5/1413 604/135 |
| 2008/0051730 | A1 * | 2/2008 | Bikovsky | A61M 5/1413 604/240 |
| 2008/0140009 | A1 * | 6/2008 | Haueter | A61B 5/14503 604/161 |
| 2008/0195049 | A1 * | 8/2008 | Thalmann | A61M 5/158 604/164.01 |
| 2008/0275407 | A1 * | 11/2008 | Scheurer | A61M 5/158 604/272 |
| 2009/0131860 | A1 * | 5/2009 | Nielsen | A61M 5/14248 604/66 |
| 2010/0217105 | A1 * | 8/2010 | Yodfat | A61B 5/14503 600/365 |
| 2010/0222743 | A1 * | 9/2010 | Frederickson | A61B 17/205 604/136 |
| 2010/0228195 | A1 * | 9/2010 | Kehr | A61B 5/151 604/131 |
| 2011/0040254 | A1 * | 2/2011 | Gyrn | A61M 5/1413 604/164.12 |
| 2011/0160655 | A1 * | 6/2011 | Hanson | A61M 5/1413 604/67 |
| 2011/0178461 | A1 * | 7/2011 | Chong | A61M 5/14248 604/151 |
| 2011/0184428 | A1 * | 7/2011 | Liniger | A61M 5/158 606/108 |
| 2012/0109062 | A1 * | 5/2012 | Lanigan | A61B 5/1427 604/164.12 |
| 2012/0245515 | A1 * | 9/2012 | Calasso | A61M 5/1413 604/67 |
| 2013/0110049 | A1 * | 5/2013 | Cronenberg | A61M 5/14248 604/180 |
| 2014/0296825 | A1 * | 10/2014 | Lemaire | A61M 5/158 604/506 |
| 2015/0080800 | A1 * | 3/2015 | Cronenberg | A61M 5/20 604/156 |
| 2015/0126926 | A1 * | 5/2015 | Giambattista | A61M 5/1454 604/135 |
| 2015/0196719 | A1 * | 7/2015 | Uchiyama | A61M 5/14248 604/156 |
| 2015/0306307 | A1 * | 10/2015 | Cole | A61M 5/14248 604/508 |
| 2016/0184512 | A1 * | 6/2016 | Marbet | A61M 5/158 604/156 |
| 2018/0085530 | A1 * | 3/2018 | Sutkin | A61M 5/3287 |

FOREIGN PATENT DOCUMENTS

| | | |
|---|---|---|
| JP | S55-76949 | 6/1980 |
| JP | S60-117641 | 6/1985 |
| JP | 2010-531197 | 9/2010 |
| WO | WO03/072172 | 9/2003 |
| WO | WO 2009/001345 | 12/2008 |
| WO | WO2009/024522 | 2/2009 |

OTHER PUBLICATIONS

Definition of knurl (Merriam-Webster Apr. 20, 2018).*
Definition of slot (Merriam Webster Dec. 20, 2018).*
International Search Report and Written Opinion in International Application No. PCT/EP2014/068597, dated Oct. 20, 2014, 8 pages.
International Preliminary Report on Patentability in International Application No. PCT/EP2014/068597, dated Mar. 8, 2016, 6 pages.
Rote Liste, "50. Hypophysen-, Hypothalamushormone, andere regulatorische Peptide u. ihre Hemmstoffe," Chapter 50, ed. 2008, 20 pages.
Japanese Office Action in Application No. 2016-539499, dated Jun. 21, 2018, 7 pages (English Translation).

* cited by examiner

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068597, filed on Sep. 2, 2014, which claims priority to European Patent Application No. 13183152.1, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

SUMMARY OF THE INVENTION

Aspects of the present invention can to provide an improved drive mechanism for a needle insertion arrangement.

The aspects can be implemented by a drive mechanism for a needle insertion arrangement according to claim 1.

Exemplary embodiments of the invention are given in the dependent claims.

According to the invention a drive mechanism for a needle insertion arrangement comprises a rotatable wheel with a notch having a closed curve geometry comprising a curved section and a linear section, wherein at least one cross beam is movably arranged and engageable to an injection needle to move it between a retracted position and an extended position, wherein the cross beam comprises a cam adapted to engage the notch.

In an exemplary embodiment the notch runs from a centre of the wheel towards a perimeter of the wheel and back to the centre.

In an exemplary embodiment the curved section is arranged as a semi-circular section.

In an exemplary embodiment the drive mechanism comprises a proximal cross beam and a distal cross beam arranged in parallel, having respective cams and independently movable along at least one linear guide.

In an exemplary embodiment at an intersection of the curved section with the linear section near the centre of the wheel the notch comprises a bulge adapted to receive both cams.

In an exemplary embodiment a spring is arranged between the cross beams biasing them apart.

In an exemplary embodiment the drive mechanism further comprises a needle retainer adapted to retain the injection needle, movable in parallel with the at least one cross beam and adapted to be engaged by the at least one cross beam.

In an exemplary embodiment the needle retainer comprises a distal prong adapted to be engaged by the distal cross beam and a proximal prong adapted to be engaged by the proximal cross beam, the distal prong and the proximal prong spaced from each other.

In an exemplary embodiment a distance between the distal prong and the proximal prong corresponds to a length of the linear section of the notch.

In an exemplary embodiment a first linear guide is arranged for guiding movements of the needle retainer.

In an exemplary embodiment a second linear guide and a third linear guide for guiding movements of the cross beams are arranged in parallel with the first linear guide.

In an exemplary embodiment the wheel is arranged between the second linear guide and the third linear guide.

In an exemplary embodiment the wheel comprises a knurl.

The drive mechanism may be applied in an insertion arrangement for moving an injection needle between a retracted position and an extended position, comprising a disposable unit, comprising a needle base, to which the needle is fixed, and the drive mechanism, wherein the needle retainer is adapted to retain the needle base.

The insertion arrangement has only limited space requirements determined by the required needle insertion depth thus allowing for low profile injection devices with a high wearing comfort. The insertion arrangement achieves high speed needle movements and exact needle guidance thus reducing pain for the patients when semi-automatically inserting and retracting the needle and increasing consumer acceptance and satisfaction. A speed profile of the needle movement may be varied by modifying the geometry of the notch. The insertion arrangement may be embodied with manual or motor powered operation. The low part count of the insertion arrangement and the low allows for an increased mechanical robustness and low manufacturing costs. The insertion arrangement is a fault-tolerant system.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
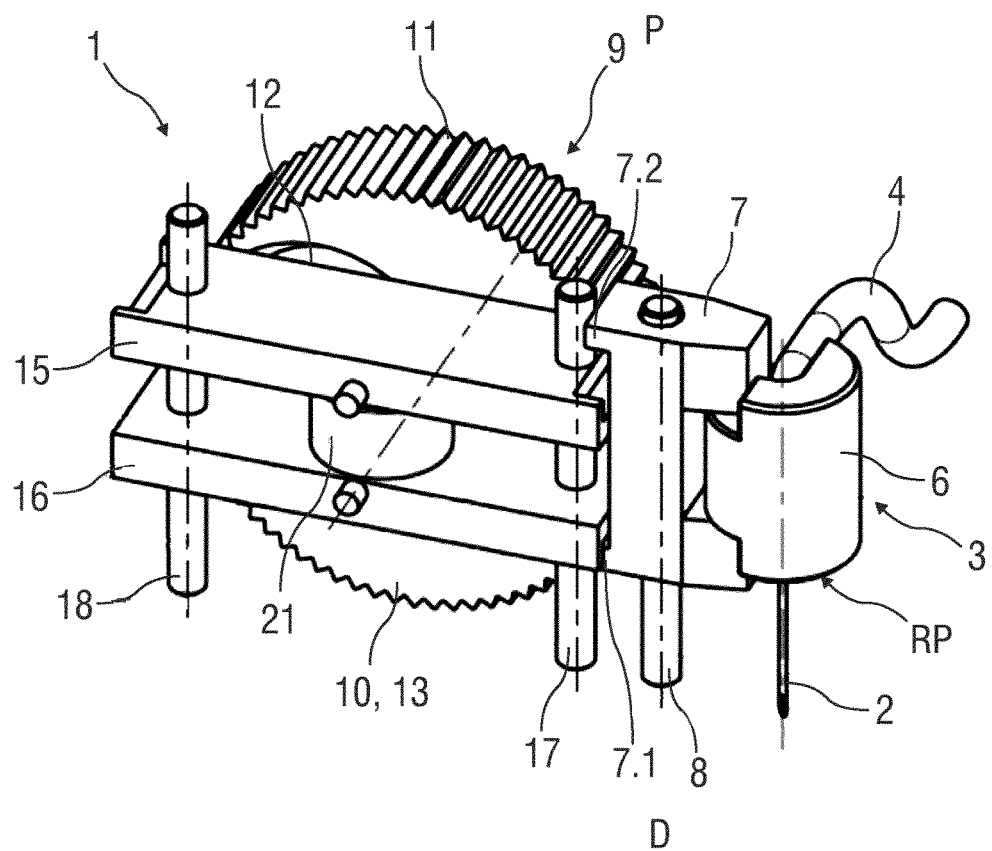
FIG. 1 is a schematic view of an exemplary embodiment of an insertion arrangement for inserting an injection needle into an injection site.
Figure 2:
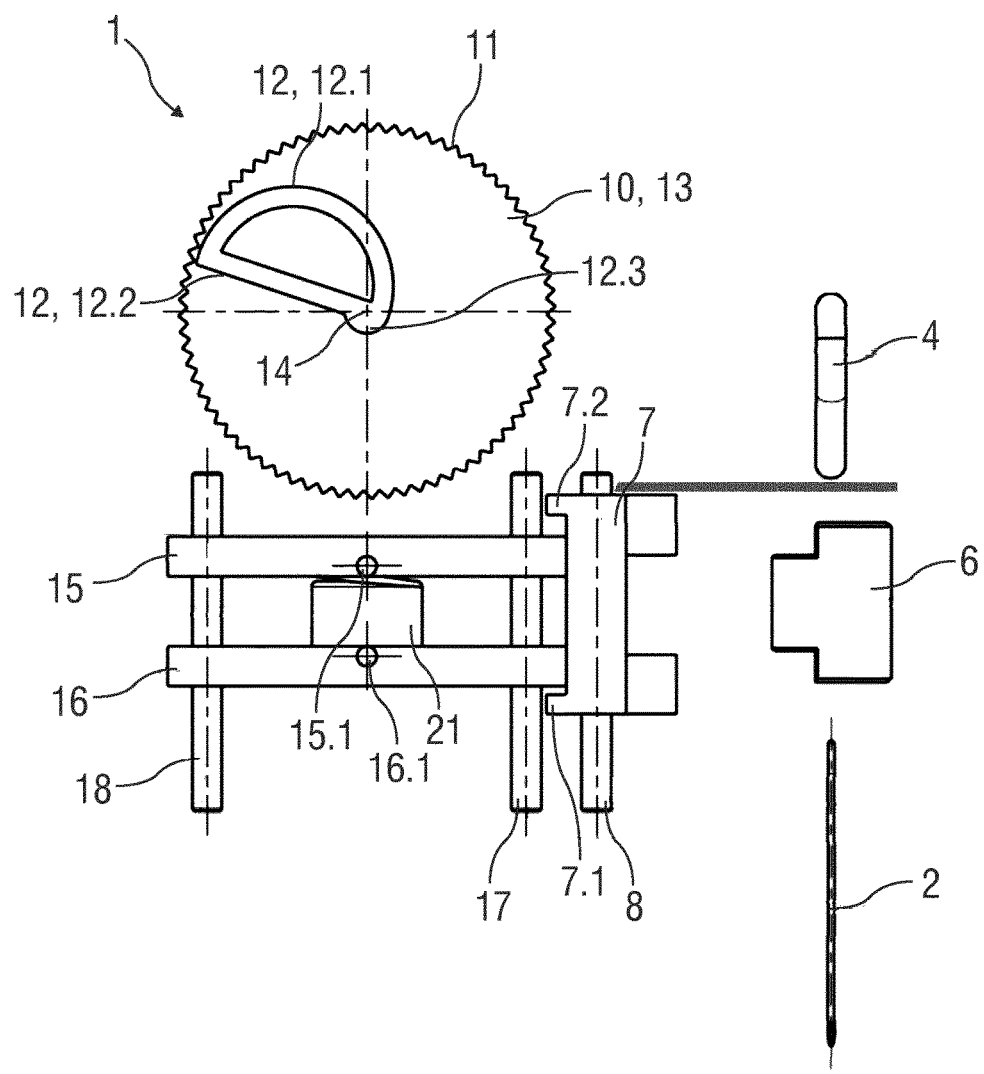
FIG. 2 is a schematic exploded view of the insertion arrangement.

FIG. 1 is a schematic view of an exemplary embodiment of an insertion arrangement 1 for automatically or semi-automatically inserting an injection needle 2 into an injection site. FIG. 2 is a related schematic exploded view. The injection may be performed manually or by a motor. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved between a retracted position RP and an extended position EP in a first linear guide 8. This linear movement corresponds to insertion of the needle 2 into the injection site, e.g. subcutaneous body tissue and removal from the injection site, respectively.

A drive mechanism 9 for the needle 2 comprises a wheel 10 with a knurl 11 for facilitating manual operation. A notch 12 having a closed curve geometry is arranged on one end face 13 of the wheel 10, wherein the notch 12 runs from a centre 14 of the wheel 10 towards the perimeter and back to the centre 14. In the illustrated embodiment the notch 12 comprises a curved section 12.1, e.g. semi-circular, and a linear section 12.2. At an intersection of the curved section 12.1 with the linear section 12.2 near the centre 14 of the wheel the notch 12 comprises a bulge 12.3. Furthermore, the drive mechanism 9 comprises a proximal cross beam 15 and a distal cross beam 16 arranged in parallel. Both cross beams 15, 16 are independently movable along a second linear guide 17 and a third linear guide 18. The second and third linear guide 17, 18 are arranged in parallel with the first linear guide 8. Each cross beam 15, 16 comprises a cam 15.1, 16.1 adapted to engage the notch 12 in the wheel 10. A spring 21 is arranged between the cross beams 15, 16 biasing them apart.

If the wheel 10 is rotated, the cams 15.1, 16.1 are guided through the notch 12, wherein one of the cams 15.1, 16.1 runs through the curved section 12.1 of the notch 12 and is thus moved towards the centre 14 of the wheel 10, where the other one of the cams 16.1, 15.1 is located. If the one of the cams 15.1, 16.1 is moved towards the centre 14 of the wheel 10 the respective cross beam 15, 16 is moved towards the other cross beam 16, 15 thereby tensioning the spring 21. If the cross beams 15, 16 have reached their minimum distance and the spring 21 is maximally compressed, the linear section 12.2 arrives in a vertical position in parallel with the linear guides 8, 17, 18. This allows the cams 15.1, 16.1 to move along the linear section 12.2 in parallel to the linear guides 8, 17, 18. Due to the compressed spring 21 one of the cross beams 15, 16 therefore moves until the related cam 15.1, 16.1 hits the outer end of the linear section 12.2. Which one of the cross beams 15, 16 moves depends on whether the linear section 12.2 points in a distal direction D or in a proximal direction P from the centre 14. If the linear section 12.2 points in the proximal direction P from the centre 14, the proximal cross beam 15 moves in the proximal direction P while the distal cross beam 16 remains in position. If the linear section 12.2 points in the distal direction P from the centre 14, the distal cross beam 16 moves in the distal direction D while the proximal cross beam 15 remains in position.

The forked needle retainer 7 comprises a distal prong 7.1 adapted to be engaged by the distal cross beam 16 and a proximal prong 7.2 adapted to be engaged by the proximal cross beam 15. A distance between the distal prong 7.1 and the proximal prong 7.2 corresponds to the length of the linear section 12.2 of the notch 12. Thus, the needle retainer 7 and the needle 2 remain in position if one of the cross beams 15, 16 is moved towards the other compressing the spring 21. As the linear section 12.2 arrives in a vertical position in parallel with the linear guides 8, 17, 18, the spring 21 relaxes forwarding the other one of the cross beams 15, 16 thus moving the needle 2 from the retracted position RP to the extended position EP or vice versa with high speed. A detent (not illustrated) may be arranged for preventing the needle retainer 7 from moving out of the retracted position RP or the extended position EP by gravity or inertial forces.

Figure 3:
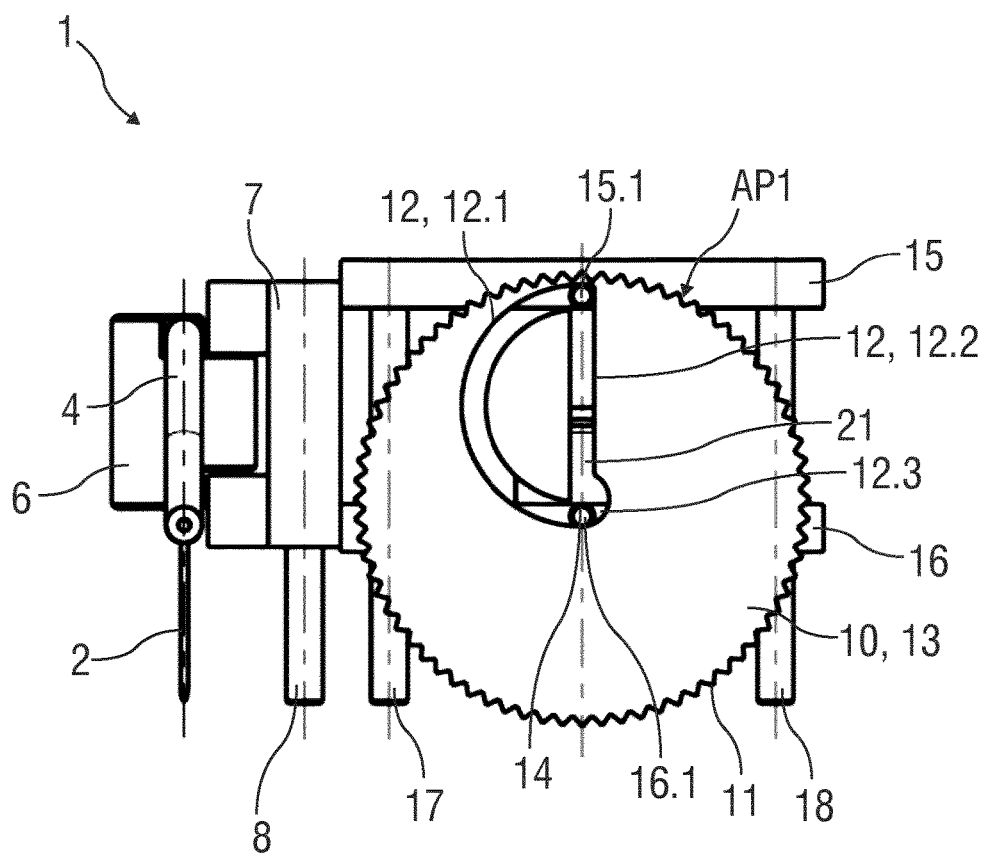
FIG. 3 is a schematic side view of the insertion arrangement in an initial position, wherein the needle is in a retracted position and wherein a wheel is in a first angular position.

A sequence of operation of the insertion arrangement 1 is as follows:

FIG. 3 is a schematic side view of the insertion arrangement 1 in an initial position. The disposable unit 3 with the needle base 6, the needle 2 and the tube 4 has been inserted in the forked needle retainer 7. The wheel 10 is in a first angular position AP1 in which the linear section 12.2 of the notch 12 is in a vertical position in parallel with the linear guides 8, 17, 18 and points in the proximal direction P from the centre 14. The proximal cross beam 15 is in a proximal position with its cam 15.1 located at the outer end of the linear section 12.2 and abuts the proximal prong 7.2 of the needle retainer 7. The distal cross beam 16 is in a central position with its cam 16.1 located at the inner end of the linear section 12.2 in the bulge 12.3 and abuts the distal prong 7.2 of the needle retainer 7. Due to the positions of the cross beams 15, 16 the needle retainer 7 and the needle 2 are in the retracted position RP.

Figure 4:
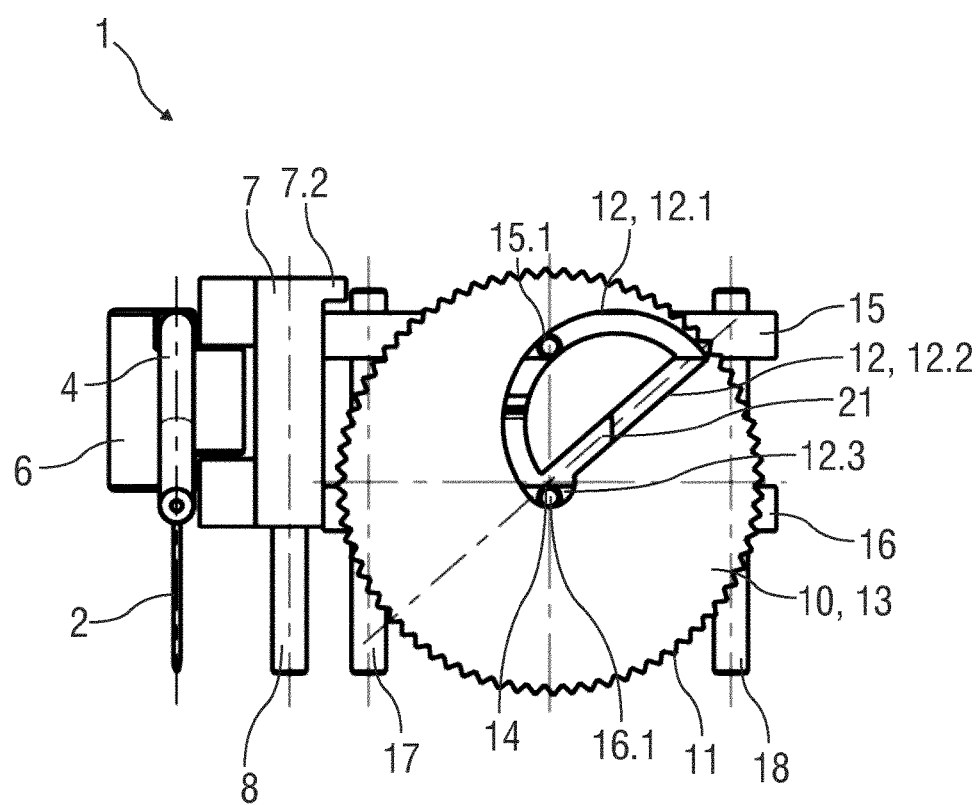
FIG. 4 is a schematic side view of the insertion arrangement during rotation of the wheel.

FIG. 4 is a schematic side view of the insertion arrangement 1 during rotation of the wheel 10. The wheel 10 is rotated clockwise by about 45° with respect to the first angular position AP1. The cam 15.1 of the proximal cross beam 15 slides along the curved section 12.1 of the notch 12 moving the proximal cross beam 15 in the distal direction D and compressing the spring 21. The proximal cross beam 15 is thus removed from the proximal prong 7.2 of the needle retainer 7. The distal cross beam 16 remains in the central position. Due to the movement of the proximal cross beam 15 a gap is created between the proximal cross beam 15 and the proximal prong 7.2 of the needle retainer 7. The needle retainer 7 and the needle 2 remain in the retracted position RP.

Figure 5:
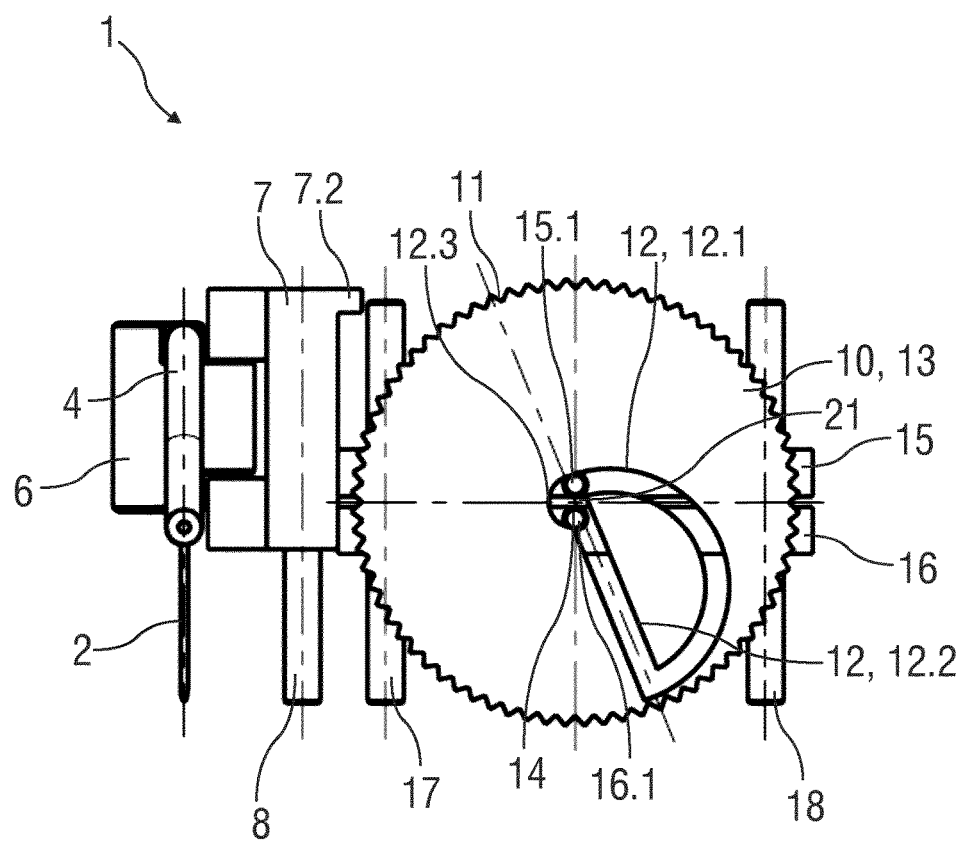
FIG. 5 is a schematic side view of the insertion arrangement during further rotation of the wheel.

FIG. 5 is a schematic side view of the insertion arrangement 1 during further rotation of the wheel 10. The wheel 10 is rotated clockwise by about 160° with respect to the first angular position AP1. The cam 15.1 of the proximal cross beam 15 still slides along the curved section 12.1 of the notch 12 moving the proximal cross beam 15 further in the distal direction D and compressing the spring 21. As the proximal cross beam 15 approaches the central position it slows down due to the position of the cam 15.1 in the curved section 12.1 until the cam 15.1 enters the bulge 12.3, which is wide enough for both cams 15.1, 16.1 at a time. At the same time the spring 21 is almost maximally compressed. The distal cross beam 16 remains in the central position. The gap between the proximal cross beam 15 and the proximal prong 7.2 of the needle retainer 7 has almost reached its maximum width. The needle retainer 7 and the needle 2 remain in the retracted position RP.

Figure 6:
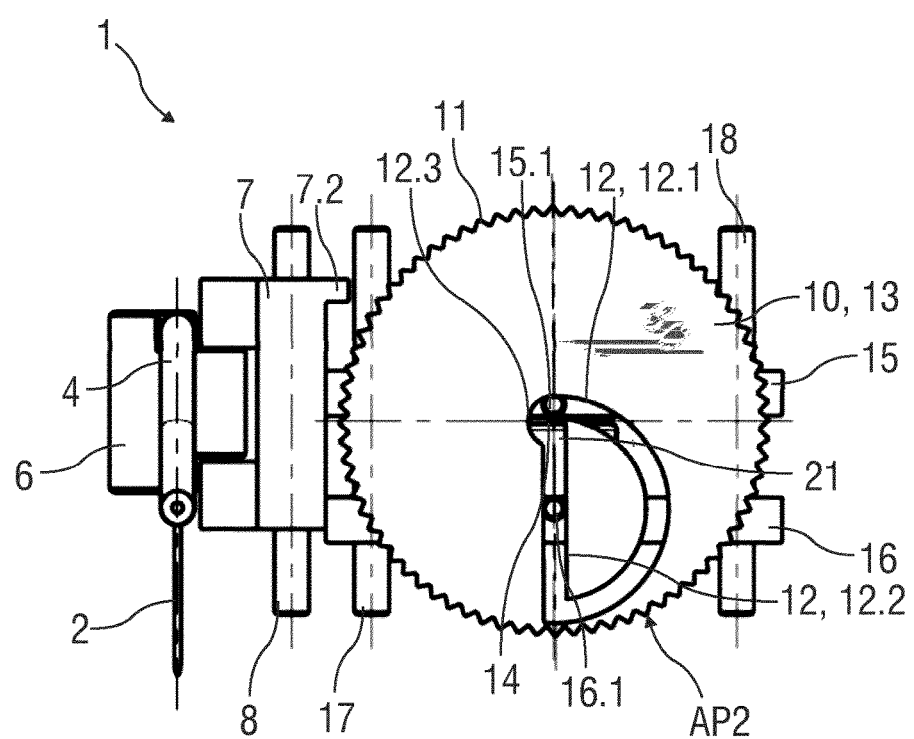
FIG. 6 is a schematic side view of the insertion arrangement, wherein the wheel has been rotated into a second angular position.

FIG. 6 is a schematic side view of the insertion arrangement 1 during further rotation of the wheel 10. The wheel 10 is rotated clockwise by about 180° with respect to the first angular position AP1 and thus reaches a second angular position AP2, in which the linear section 12.2 of the notch 12 is in a vertical position in parallel with the linear guides 8, 17, 18 and points in the distal direction D from the centre 14. This releases the cam 16.1 of the distal cross beam 16 allowing the spring 21 to move the distal cross beam 16 in the distal direction D. This movement is performed with relatively high speed depending on the force of the compressed spring 21. The cam 15.1 of the proximal cross beam 15 is retained in the bulge 12.3 thus keeping the proximal cross beam 15 in the central position. As the distal cross beam 16 moves it takes the needle retainer 7 with it moving it in the distal direction D and reducing the width of the gap between the proximal cross beam 15 and the proximal prong 7.2 of the needle retainer 7.

Figure 7:
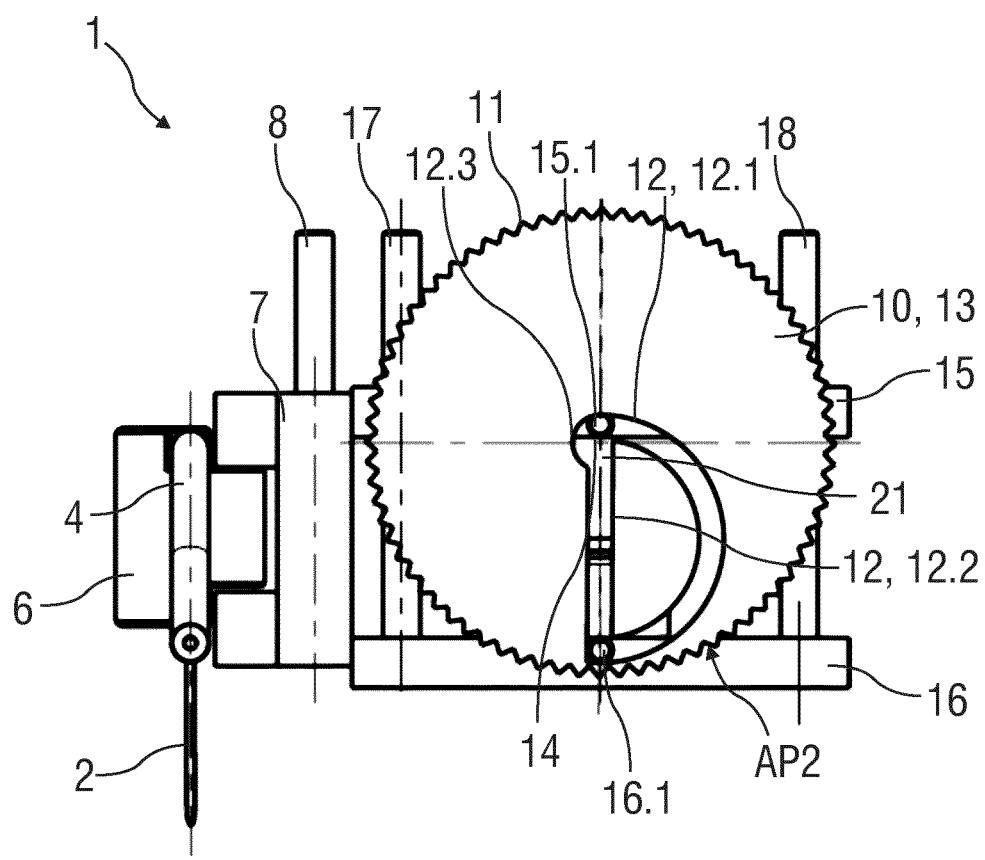
FIG. 7 is a schematic side view of the insertion arrangement with the needle moved into an extended position.

FIG. 7 is a schematic side view of the insertion arrangement 1 with the cam 16.1 of the distal cross beam 16 having reached the outer end of the linear section 12.2. The distal cross beam 16 is moved into a distal position and has taken along the distal prong 7.1 of the needle retainer 7 moving the needle retainer 7 and the needle 2 into the extended position EP in order to rapidly insert the needle 2 into an injection site, e.g. subcutaneous body tissue. The gap has been closed by the proximal prong 7.2 abutting the proximal cross beam 15.

Figure 8:
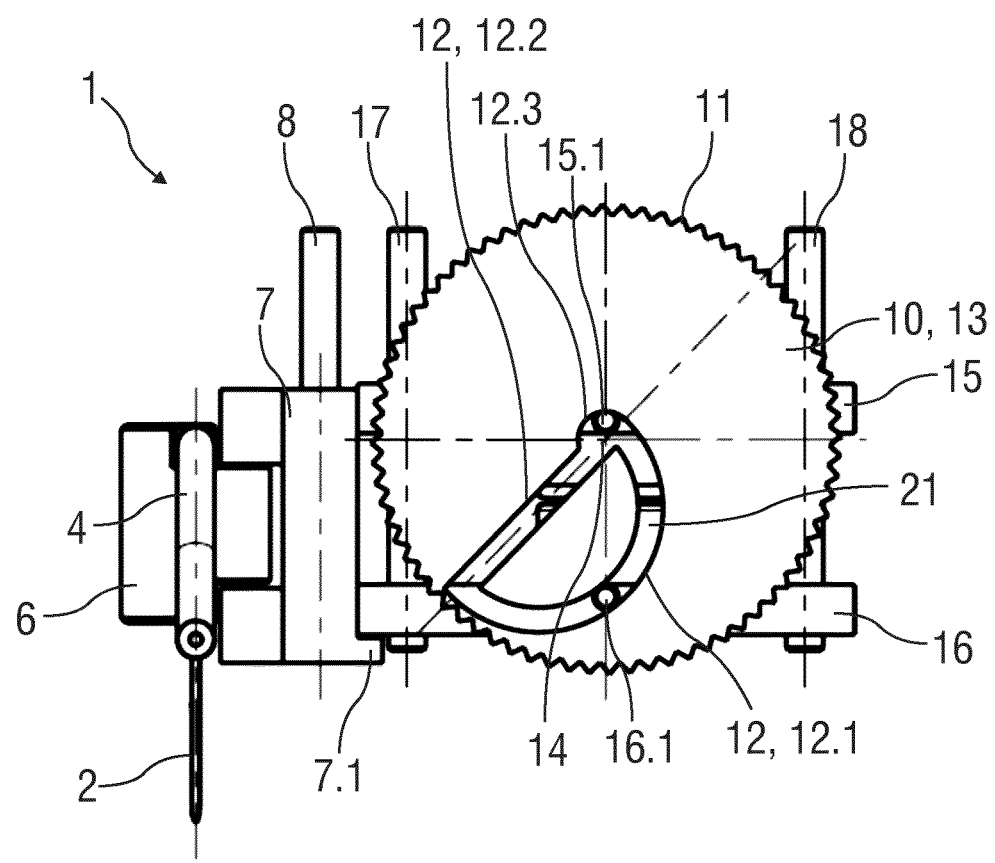
FIG. 8 is a schematic view of the insertion arrangement during further rotation of the wheel.

FIG. 8 is a schematic view of the insertion arrangement 1 during further rotation of the wheel 10. The wheel 10 is rotated clockwise by about 45° with respect to the second angular position AP2. The cam 16.1 of the distal cross beam 16 slides along the curved section 12.1 of the notch 12 moving the distal cross beam 16 in the proximal direction P and compressing the spring 21. The distal cross beam 16 is thus removed from the distal prong 7.1 of the needle retainer 7. The proximal cross beam 15 remains in the central position. Due to the movement of the distal cross beam 16 a gap is created between the distal cross beam 16 and the distal prong 7.1 of the needle retainer 7. The needle retainer 7 and the needle 2 remain in the extended position EP.

Figure 9:
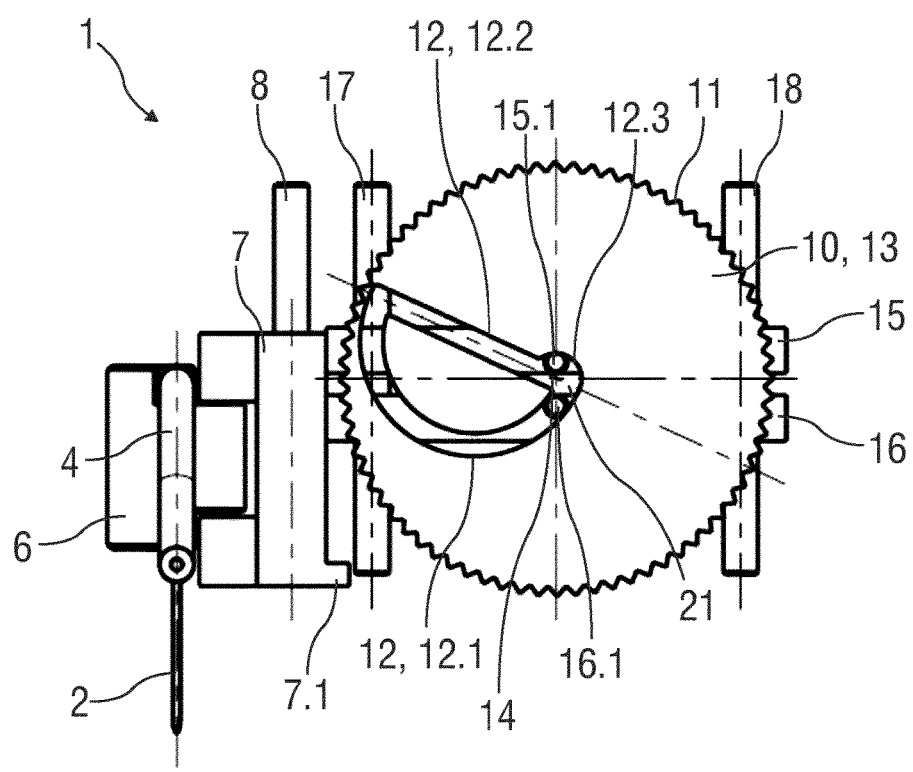
FIG. 9 is a schematic view of the insertion arrangement during further rotation of the wheel.

FIG. 9 is a schematic view of the insertion arrangement 1 during further rotation of the wheel 10. The wheel 10 is rotated clockwise by about 115° with respect to the second angular position AP2. The cam 16.1 of the distal cross beam 16 still slides along the curved section 12.1 of the notch 12 moving the distal cross beam 16 further in the proximal direction P and compressing the spring 21. As the distal cross beam 16 approaches the central position it slows down due to the position of the cam 16.1 in the curved section 12.1 until the cam 16.1 enters the bulge 12.3.

At the same time the spring 21 is almost maximally compressed. The proximal cross beam 15 remains in the central position. The gap between the distal cross beam 16 and the distal prong 7.1 of the needle retainer 7 has almost reached its maximum width. The needle retainer 7 and the needle 2 remain in the extended position EP.

Figure 10:
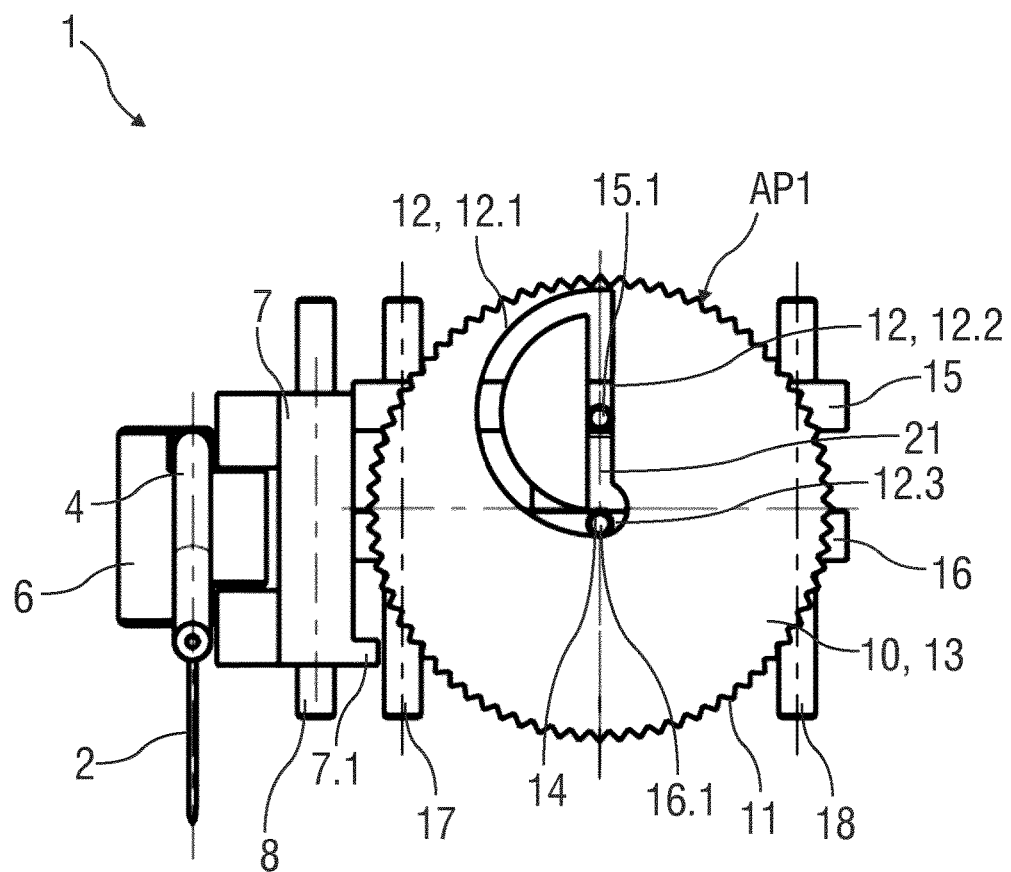
FIG. 10 is a schematic side view of the insertion arrangement with the wheel rotated into the first angular position.

FIG. 10 is a schematic side view of the insertion arrangement 1 during further rotation of the wheel 10. The wheel 10 is rotated clockwise by about 180° with respect to the second angular position AP2 and thus reaches the first angular position AP1, in which the linear section 12.2 of the notch 12 is in a vertical position in parallel with the linear guides 8, 17, 18 and points in the proximal direction P from the centre 14. This releases the cam 15.1 of the proximal cross beam 15 allowing the spring 21 to move the proximal cross beam 15 in the proximal direction P. This movement is performed with relatively high speed depending on the force of the compressed spring 21. The cam 16.1 of the distal cross beam 16 is retained in the bulge 12.3 thus keeping the distal cross beam 16 in the central position. As the proximal cross beam 15 moves it takes the needle retainer 7 with it moving it in the proximal direction P and reducing the width of the gap between the distal cross beam 16 and the distal prong 7.1 of the needle retainer 7.

Figure 11:
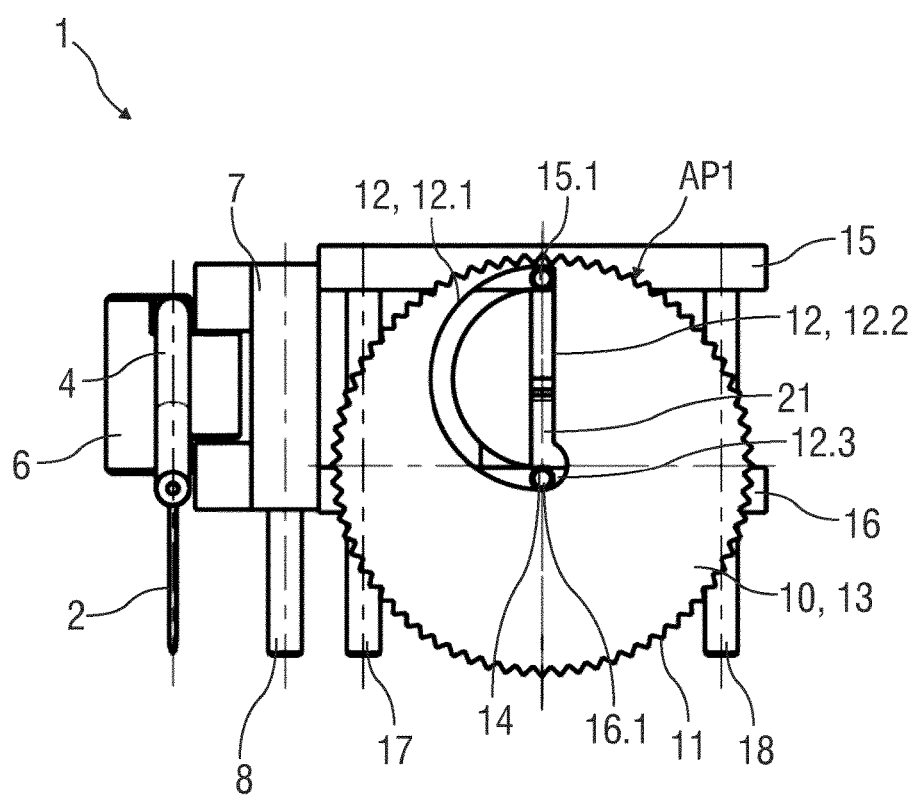
FIG. 11 is a schematic side view of the insertion arrangement with the needle moved into the retracted position.

FIG. 11 is a schematic side view of the insertion arrangement 1 with the cam 15.1 of the proximal cross beam 15 having reached the outer end of the linear section 12.2. The proximal cross beam 15 is moved into the proximal position and has taken along the proximal prong 7.2 of the needle retainer 7 moving the needle retainer 7 and the needle 2 into the retracted position RP. The gap has been closed by the distal prong 7.1 abutting the distal cross beam 16.

In an alternative embodiment the geometry of the notch 12, in particular the curved section 12.1 may be modified to adapt the process of tensioning the spring 21 to the requirements of the respective application. For this purpose the semi-circular section 12.1 may be replaced by a curved section having a different shape.

In an alternative embodiment the wheel 10 may be a gear wheel adapted to be driven by a motor.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 insertion arrangement
2 needle
3 disposable unit
4 tube
6 needle base
7 needle retainer
7.1 distal prong
7.2 proximal prong
8 first linear guide
9 drive mechanism
10 wheel
11 knurl
12 notch
12.1 curved section
12.2 linear section
12.3 bulge
13 end face
14 centre
15 proximal cross beam
15.1 cam
16 distal cross beam
16.1 cam
17 second linear guide
18 third linear guide
21 spring
AP1 first angular position
AP2 second angular position
D distal direction
EP extended position
P proximal direction
RP retracted position

The invention claimed is:

1. A drive mechanism for a needle insertion arrangement of an injection device, the drive mechanism comprising:

a rotatable wheel with a notch formed as a slot within the rotatable wheel and having a closed curve geometry comprising:
  a curved section, and
  a linear section; and
at least one cross beam movably arranged and engageable to an injection needle to move the injection needle between a retracted position and an extended position, wherein the at least one the cross beam comprises a cam adapted to engage the notch, and wherein the notch runs from a center of the rotatable wheel towards a perimeter of the rotatable wheel and back to the center.

2. A drive mechanism according to claim 1, wherein the curved section comprises a semi-circular section.

3. A drive mechanism according to claim 1, wherein the at least one cross beam comprises a proximal cross beam and a distal cross beam arranged in parallel, wherein the cam is a proximal cross beam cam, the proximal cross beam having the proximal cross beam cam, the distal cross beam having a distal cross beam cam, the proximal cross beam cam and the distal cross beam cam independently movable along at least one linear guide.

4. A drive mechanism according to claim 3, wherein at an intersection of the curved section with the linear section near the center of the rotatable wheel, the notch comprises a bulge adapted to receive the proximal cross beam cam and the distal cross beam cam.

5. A drive mechanism according to claim 3, wherein a spring is arranged between the proximal cross beam and the distal cross beam biasing the proximal cross beam and the distal cross beam apart.

6. A drive mechanism according to claim 1, further comprising a needle retainer adapted to retain the injection needle, movable in parallel with the at least one cross beam and adapted to be engaged by the at least one cross beam.

7. A drive mechanism according to claim 6, wherein the at least one cross beam comprises a proximal cross beam and a distal cross beam, wherein the needle retainer comprises a distal prong adapted to be engaged by the distal cross beam and a proximal prong adapted to be engaged by the proximal cross beam, the distal prong and the proximal prong spaced from each other.

8. A drive mechanism according to claim 7, wherein a distance between the distal prong and the proximal prong corresponds to a length of the linear section of the notch.

9. A drive mechanism according to claim 7, wherein a first linear guide is arranged for guiding movements of the needle retainer.

10. A drive mechanism according to claim 3, wherein a second linear guide and a third linear guide for guiding movements of the proximal cross beam and the distal cross beam are arranged in parallel with the first linear guide.

11. A drive mechanism according to claim 10, wherein the rotatable wheel is arranged between the second linear guide and the third linear guide.

12. A drive mechanism according to claim 1, wherein the rotatable wheel comprises a knurl.

13. An insertion arrangement for moving an injection needle between a retracted position and an extended position, the insertion arrangement comprising:
  a disposable unit comprising a needle base to which the injection needle is fixed; and
  a drive mechanism comprising:
    a rotatable wheel with a notch having a closed loop-shaped, closed curve geometry comprising:
      a curved section, and
      a linear section; and
    at least one cross beam movably arranged and engageable to the injection needle to move the injection needle between the retracted position and the extended position, wherein at least one the cross beam comprises a cam adapted to engage the notch,
  wherein a needle retainer is adapted to retain the needle base,
  wherein the at least one cross beam comprises a proximal cross beam and a distal cross beam arranged in parallel, and
  wherein the cam is a proximal cross beam cam, the proximal cross beam having the proximal cross beam cam, the distal cross beam having a distal cross beam cam, the proximal cross beam cam and the distal cross beam cam independently movable along at least one linear guide.

14. The insertion arrangement according to claim 13, wherein the notch runs from a center of the wheel towards a perimeter of the wheel and back to the center.

15. The insertion arrangement according to claim 13, wherein the curved section comprises a semi-circular section.

16. The insertion arrangement according to claim 13, wherein at an intersection of the curved section with the linear section near the center of the wheel, the notch comprises a bulge adapted to receive the proximal cross beam cam and the distal cross beam cam.

17. The insertion arrangement according to claim 13, wherein a spring is arranged between the proximal cross beam and the distal cross beam biasing the proximal cross beam and the distal cross beam apart.

18. An auto-injector comprising:
  an insertion arrangement for moving an injection needle between a retracted position and an extended position, the insertion arrangement comprising:
    a disposable unit comprising a needle base to which the needle is fixed; and
    a drive mechanism comprising:
      a rotatable wheel with a notch formed as a slot within the rotatable wheel and having a closed curve geometry comprising:
        a curved section, and
        a linear section;
      at least one cross beam movably arranged and engageable to the injection needle to move the injection needle between the retracted position and the extended position, wherein at least one the cross beam comprises a cam adapted to engage the notch, wherein the notch runs from a center of the rotatable wheel towards a perimeter of the rotatable wheel and back to the center,
    wherein a needle retainer is adapted to retain the needle base; and
    a drug container coupled to the injection needle, the drug container carrying a medicament consisting of at least one pharmaceutically active compound.

19. Drive mechanism for a needle insertion arrangement of an injection device, the drive mechanism comprising:
  a rotatable wheel with a notch having a closed curve geometry comprising:
    a curved section, and
    a linear section;
  at least one cross beam movably arranged and engageable to an injection needle to move the injection needle between a retracted position and an extended position, wherein at least one the cross beam comprises a cam adapted to engage the notch;

a needle retainer adapted to retain the injection needle, movable in parallel with the at least one cross beam and adapted to be engaged by the at least one cross beam, wherein the at least one cross beam comprises a proximal cross beam and a distal cross beam, wherein the needle retainer comprises a distal prong adapted to be engaged by the distal cross beam and a proximal prong adapted to be engaged by the proximal cross beam, the distal prong and the proximal prong spaced from each other, wherein a distance between the distal prong and the proximal prong corresponds to a length of the linear section of the notch.

* * * * *

UNITED STATES PATENT AND TRADEMARK OFFICE
CERTIFICATE OF CORRECTION

PATENT NO.         : 10,369,278 B2
APPLICATION NO.    : 14/916667
DATED              : August 6, 2019
INVENTOR(S)        : Philippe Nzike et al.

Page 1 of 1

It is certified that error appears in the above-identified patent and that said Letters Patent is hereby corrected as shown below:

In the Claims

Column 11, Line 9, Claim 1, after "one", delete "the"

Column 12, Line 4, Claim 13, after "wherein", insert --the--

Column 12, Line 4, Claim 13, after "one", delete "the"

Column 12, Line 47, Claim 18, after "wherein", insert --the--

Column 12, Line 47, Claim 18, after "one", delete "the"

Column 12, Line 66, Claim 19, after "wherein", insert --the--

Column 12, Line 66, Claim 19, after "one", delete "the"

Signed and Sealed this
Eighteenth Day of February, 2020

Andrei Iancu
*Director of the United States Patent and Trademark Office*